United States Patent [19]
Tigyi et al.

[11] Patent Number: 4,882,336
[45] Date of Patent: Nov. 21, 1989

[54] METHOD AND PHARMACEUTICAL COMPOSITION FOR TREATING LEUKOENCEPHALITIC DEMYELINIZATION CLINICAL PATTERNS OF AUTOIMMUNE ORIGIN, PARTICULARLY MULTIPLE SCLEROSIS

[75] Inventors: Gabor Tigyi, Irvine, Calif.; Bela Bozoky; Zsuzsanna Szegvari, both of Szeged, Hungary; Tibor Frank, Budapest, Hungary; Gyorgy Hajos, Budapest, Hungary; Laszlo Szporny, Budapest, Hungary; Lilla Forgacs, Budapest, Hungary

[73] Assignee: Richter Gedeon Vegyeszeti Gyar Rt., Budapest, Hungary

[21] Appl. No.: 233,076

[22] Filed: Aug. 17, 1988

[30] Foreign Application Priority Data

Aug. 26, 1987 [HU] Hungary .............................. 3753/87

[51] Int. Cl.⁴ ............................................. A61K 31/44
[52] U.S. Cl. .................................................... 514/283
[58] Field of Search .......................................... 514/283

[56] References Cited

U.S. PATENT DOCUMENTS 4,382,936  5/1983  Katsube et al. ..................... 514/283

Primary Examiner—Douglas W. Robinson
Assistant Examiner—Zohreh A. Fay
Attorney, Agent, or Firm—Herbert Dubno; Jonathan Myers

[57] ABSTRACT

A method of treating demyelinization clinical patterns of autoimmune origin, particularly multiple sclerosis. The pharmaceutical composition makes use of ethyl (+)-apovincaminate as the active ingredient.

4 Claims, 2 Drawing Sheets

METHOD AND PHARMACEUTICAL COMPOSITION FOR TREATING LEUKOENCEPHALITIC DEMYELINIZATION CLINICAL PATTERNS OF AUTOIMMUNE ORIGIN, PARTICULARLY MULTIPLE SCLEROSIS

FIELD OF THE INVENTION

The invention relates to a method for treating demyelinization clinical patterns of autoimmune origin, particularly multiple sclerosis.

The invention further relates to a pharmaceutical composition which is useful for treating demyelinization clinical patterns of autoimmune origin, particularly the multiple sclerosis.

The invention also relates to the use of ethyl (+)-apovincaminate for the preparation of a pharmaceutical composition which is useful for treating demyelinization clinical patterns of autoimmune origin, particularly multiple sclerosis.

BACKGROUND OF THE INVENTION

It is known that, due to its action promoting the brain circulation and improving the oxygen utilization of cerebral tissues, ethyl (+)-apovincaminate (Cavinton ® vinpocetin) can therapeutically be used with success as a cerebral vasodilator (see e.g. British patent specification No. 1,405,127).

DESCRIPTION OF THE INVENTION

Based on our results obtained in animal experiments, we have surprisingly found that ethyl (+)-apovincaminate can be used for treating demyelinization clinical patterns of autoimmune origin, particularly multiple sclerosis.

Ethyl (+)-apovincaminate can be prepared in a known way by nitrosating an octahydroindoloquinolizine derivative and treating the hydroxyimino-octahydroindoloquinolizine derivative obtained by an acid (British patent specification No. 2,102,415). Alternatively, ethyl (+)-apovincaminate can be prepared by using any process disclosed e.g. in German Pat. Nos. 2,813,015 and 2,944,036; Japanese Pat. No. 1,237,552; British patent specifications Nos. 2,036,744, 2,086,886 and 2,102,415; U.S. Pat. No. 4,400,514; as well as Hungarian Pat. No. 184,482.

The multiple sclerosis and other leukoencephalitic demyelinization clinical patterns of autoimmune origin such as e.g. perivenous encephalomyelitis (encephalomyelitis perivenosa) and acute haemorrhagic leukoencephalitis are diseases affecting the white matter of the human central nervous system. No therapeutic method has been known to the present which could be used for the successful treatment of this group of diseases.

Until now, the therapeutic efforts have been grouped in two categories: these are antiinflammatory-immunosuppressive therapies on the one part and supportive therapies for stabilizing the status of the patient on the other part. In the antiinflammatory therapy, steroids abolishing the inflammation, cytostatics such as Cyclophosphamide or Azathioprine as well as the antibiotic Cyclosporin A as immunosuppressive agent and combinations of these drugs are usually employed. Similarly, other immunomodulatory treatment methods, aimed at influencing the effector phase of the immune response, e.g. treatment with α-interferon, whole-body irradiation (by X-rays) and the hyperbaric oxygen therapy may be used.

By supportive therapy such therapeutic processes are meant which are aimed to preserve the status of the patient. The sphere of these treatment methods is wide and includes e.g. vitamin therapy ($B_{12}$, $B_6$), various physicotherapeutic methods and dietetic therapy enriched of essential fatty acids.

Based on the results obtained in animal experiments, we have found that ethyl (+)-apovincaminate is useful for treating demyelinization clinical patterns of autoimmune origin, particularly multiple sclerosis. The ethyl (+)-apovincaminate can be used either directly or in a pharmaceutical composition containing it together with any of the known agents used in the antiinflammatory-immunosuppressive therapeutic methods mentioned hereinbefore such as antiinflammatory steroids or cytostatics; or by using them in separate pharmaceutical compositions one after the other. The ethyl (+)-apovincaminate can be used together with any of the immunomodulatory treatment methods described hereinbefore or by use of a sequential treatment wherein the methods are applied separately one after the other. It can be used together with any of the supportive therapies as supplementation.

As a test model of the human demyelinization diseases, acute experimental allergic encephalomyelitis was chosen which is an artificially developed clinical status in animals, mainly in rodents, e.g. mice, rats or guinea-pigs [Neurochemical Res. 6 (1981)]. Several methods are known for the evaluation of the symptoms developed [J. Immunol. 132, 191 (1984)]. Usually, the walking, the defecation, histological alterations and changes of the immunological parameters of the animals are observed.

The investigations were carried out as described hereinafter.

50 µg of purified basic myelin protein and 100 µg of killed Mycobacterium tuberculosis were dissolved in 50 µl of sterile physiological saline solution buffered at pH 7 to 7.2 with disodium hydrogen phosphate and sodium dihydrogen phosphate and the solution was emulsified with 50 µl of Freund's complete adjuvant. The emulsion obtained was inoculated in the day 0 into the left posterior paw of inbred R9 and R9 albino guinea-pigs of both sexes, with 300 g of body-weight, which have been kept under standardized animal house conditions. Under the effect of the immunization, the animals became ill in the day 12 following the immunization and the death rate in the group of the controls amounted to 90% in the day 14. The treatment was started simultaneously with the inoculation in the day 0. During the treatment groups of 3 to 5 animals were daily once intraperitoneally (i.p.) treated by ethyl (+)-apovincaminate dissolved in an ascorbic acid solution of 20% in daily doses of 0.25, 2.5 and 12.5 mg/kg, respectively. The survival of the animals was recorded as a most complex measure of the drug therapy used which expresses the efficiency as well as any harmful side effects of the therapy. The average survival time was determined by calculating the arithmetical mean value from the survival times of the individuals of the treated groups. The experiment lasted 21 days since a survival of 20 days is considered as successful survival of the acute inflammation in the literature. The results are summarized in Table I.

TABLE I

Survival in days of guinea-pigs suffering from acute experimental allergic encephalomyelitis during an experimental period of 21 days

| Treatment | | |
|---|---|---|
| Substance | Dose mg/kg/day i.p. | Time of survival days |
| Control (physiological saline) | | 12.0 |
| Ethyl (+)-apovincaminate | 0.25 | 17.4 |
| | 2.50 | 20.4 |
| | 12.50 | 20.0 |

It is obvious from Table I that the animals were practically protected from the lethal outcome of acute experimental encephalomyelitis by using ethyl (+)-apovincaminate.

After the termination of the experimental period, the animals were killed by ether overdose, dissected, then four regions of the central nervous system (frontally sectioned brain slices, brain stem-cerebellum, lower and upper segment of the spinal cord) were subjected to histological examination.

SPECIFIC DESCRIPTION

Figure 1A:
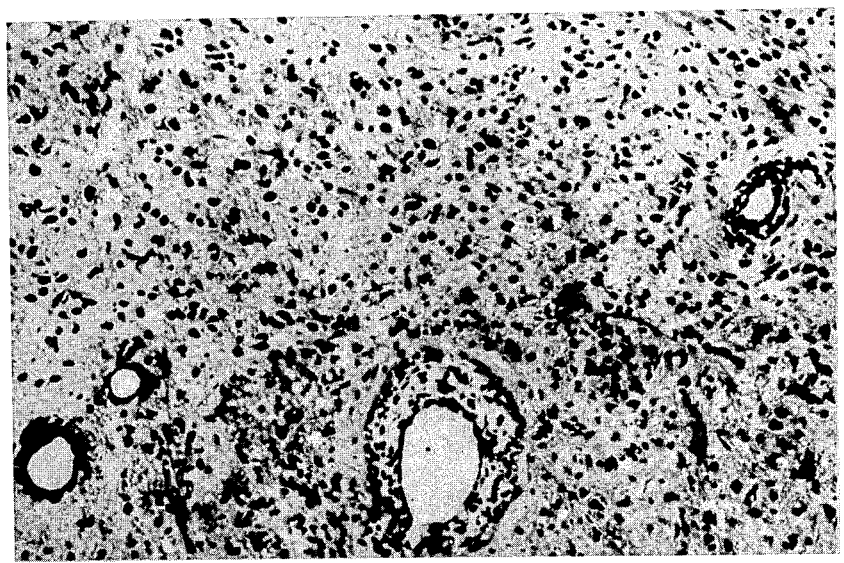
FIGS. 1a, 1b, 1c and 2 show tissue micrographs of the histological examination.
Figure 1B:
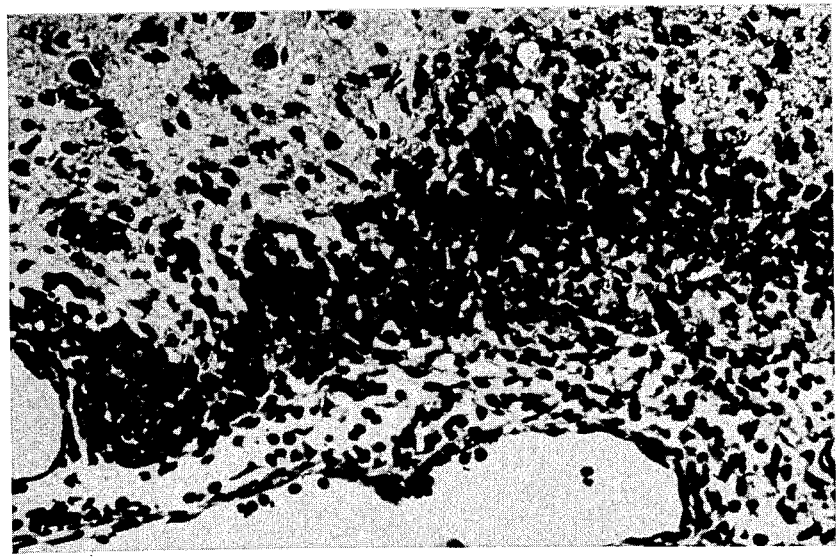
Figure 1C:
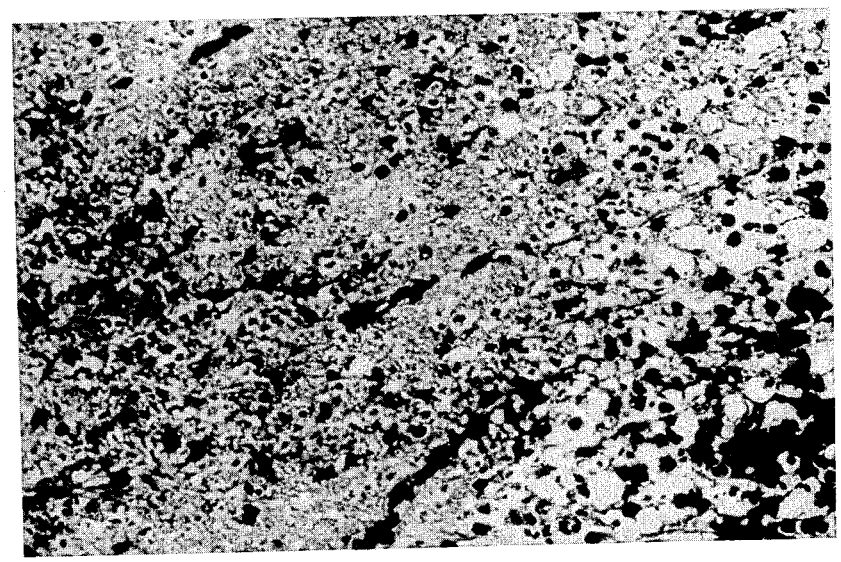
Figure 2:
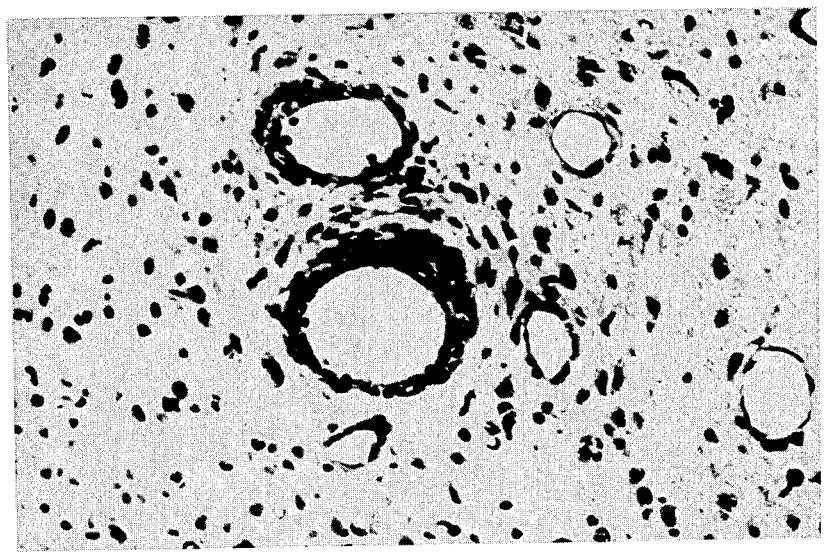

In the case of the control animals inflammation and accumulation of microglia cells were observed in the brain (FIG. 1a), the brain stem (FIG. 1b) and in the spinal cord with damage to the neurons and demyelinization effects (FIG. 1c).

In sharp contradistinction, in the case of the animals treated with ethyl (+)-apovincaminate the inflammation was reduced substantially to a perivascular localization due to which the walls of the blood vessels became thickened (FIG. 3). There is no less or only very limited loss of neurons in the gray matter, or demyelinization in the white matter which is proved by FIG. 3 showing a very limited number of inflamed cells and microglia cells, except at perivascular part, compared to the control.

The more accurate determination of the numerical change and the ratio change of the inflammated cells and microglia cells, furthermore the explanation of the apparent histological changes could be the subject of further neuropathological examinations.

On the basis of the above facts it can be stated that ethyl (+)-apovincaminate extends the life span of animals suffering in acute experimental allergic encephalomyelitis to a high degree, and also decreases the clinical differences and simultaneously the histological differences connected therewith. The inflammation of the central nervous system did not damage most of the gray and white matter and appeared in the form of perivascular localization in the animals treated effectively.

A comparative pharmacological study was also carried out by using Dexamethasone, a steroidal antiinflammatory drug employed for treating demyelinization clinical patterns of autoimmune origin, especially multiple sclerosis. This study was performed as described above, except that the treatment was started on outbred (and not inbred) guinea-pigs one day before the immunization and the daily doses were administered in two portions being possibly distant from each other, e.g. in the morning and in the afternoon. The solvent for Dexamethasone, i.e. physiological saline solution, and the solvent for ethyl (+)-apovincaminate, i.e. a tartaric acid solution of 0.75%, were used as controls. The treatment was carried out by using ethyl (+)-apovincaminate dissolved in tartaric acid solution of 0.75%, whereas a physiological saline solution of Dexamethasone was used as reference. The results of the treatments are summarized in Table II. In this Table, the substances used for the treatments, the number of the animals treated and the time of appearance of the neurological symptoms are shown, which latter means the time, when the first neurological symptoms, usually ataxia, appeared on a given animal. These values were averaged for the animals receiving an identical treatment and the average value is shown in Table II. In the column "death", the average number of days from immunization up to the death of the animals is indicated. The number 21 means that no death occurred within the 21 day study.

In the column of "survival", the percentage of treated animals surviving up to the end of the study, i.e. surviving for 21 days, is shown. The results obtained on the animals treated with ethyl (+)-apovincaminate were compared to the results obtained with a tartaric acid solution of 0.75%, being the solvent for ethyl (+)-apovincaminate, as control; the data of the animals treated with Dexamethasone were compared to the results obtained with physiological saline solution, being the solvent for Dexamethasone as control.

The difference between the time of appearance of the symptoms and the time of death was statistically insignificant in both control groups treated with either a 0.75% tartaric acid solution or physiological saline solution; thus, the course of the disease was practically identical in these groups.

TABLE II

Effect of ethyl (+)-apovincaminate on the acute experimental allergic encephalomyelitis of guinea-pigs

| Treatment | | | | | |
|---|---|---|---|---|---|
| Substance | Dose (mg/kg/day i.p. in 2 portions) | No. of treated animals (pc.) | Appearance of symptoms (day) | Death (day) | Survival (%) |
| 0.75% tartaric acid solution (control) | | 20 | 15.1 | 15.7 | 25 |
| Ethyl (+)-apovincaminate | 10.0 | 20 | 20.5 | 20.7 | 90 |
| | 12.5 | 15 | 20.6 | 20.8 | 93 |
| | 15.0 | 13 | 19.9 | 20.2 | 85 |
| Physiological saline solution (control) | | 20 | 14.7 | 15.2 | 25 |
| Dexamethasone (reference) | 10.0 | 5 | 15.2 | 17.0 | 20 |
| | 15.0 | 5 | 17.8 | 19.6 | 60 |

It is obvious from Table II that, on the one hand, not more than 25% of 40 control animals survived whereas 85 to 93% (depending on the dose used) of the animals treated with ethyl (+)-apovincaminate survived, i.e. the decrease in the number of deaths was significant. On the other hand, when using ethyl (+)-apovincaminate in the given doses, the appearance of symptoms was significantly delayed; thus, the treatment can be considered to be successful, i.e. the symptoms did not appear even on the last day of the 21 days' treatment period, or, only in 2 cases between the day 19 and 20 of the treatment. Thus, the survival was nearly 100%. By contrast, in the case of treatment with Dexamethasone, a steroidal anti-inflammatory drug most frequently used for treating this disease, the symptoms already appeared on day 15 of the treatment; the percentage of survival was not increased by using a 10 mg/kg dose; and the appearance of the symptoms was not significantly delayed but the death was inhibited by a 15 mg/kg dose, however, in the latter case the known side effects of steroids strongly manifested themselves.

A further important difference consists in that no toxic symptoms occurred during the treatment with ethyl (+)-apovincaminate whereas on using Dexamethasone, the body-weight of the animals was enlarged by 60 to 70 g due to the water retention and they became unprotected against microorganisms. Thus, skin-mycosis occurred on 2 out of 5 animals, 1 died due to peritonitis without any neurological symptom and a beginning peritonitis was observed on 1 surviving animals during the dissection. Thus, the animals could be treated with ethyl (+)-apovincaminate for longer periods whereas, due to the immunosuppressive effect, lethal infections would be expected by using Dexamethasone.

The ethyl (+)-apovincaminate as active ingredient can be transformed to pharmaceutical compositions useful for the treatment of leukoencephalitic demyelinization clinical patterns of autoimmune origin, particularly multiple sclerosis by mixing it with known pharmaceutically acceptable, inert, non-toxic, solid or liquid carriers and/or other additives useful for enteral or parenteral administration. Suitable carriers are e.g. water, gelatine, glycerol, ethanol, lactose, cetyl alcohol, mannitol, silicic acid, carboxymethyl cellulose, alginates, polyvinylpyrrolidone, galactose, starch, pectin, magnesium stearate, stearic acid, sorbitol, kaolin, polyethylene glycol, fatty acid esters, talc, vegetable oils such as peanut oil or olive oil and the like. The active ingredient may be transformed to usual pharmaceutical compositions, e.g. solid forms (e.g. rounded or edged tablets, granulates, capsules such as hard gelatine capsules, pills, suppositories and the like) or liquid forms (e.g. oily or aqueous solutions, suspensions, emulsions, syrups, soft gelatine capsules, injectable oily or aqueous solutions or suspensions and the like). The amount of the solid carrier may be varied within wide limits, preferably it weighs between 25 mg and 1 g. The compositions according to the invention may contain also commonly used pharmaceutical additives, e.g. preservatives, salts for adjusting the osmotic pressure, surfactants, buffers, dyeing, aromatizing and flavouring agents. Furthermore, the compositions may optionally contain other therapeutically active compounds which are suitable to treat demyelinization clinical patterns of autoimmune origin. The compositions are conveniently prepared in the form of dosage units corresponding to the desired route of administration, e.g. to enteral or parenteral (intramuscular, intraperitoneal, subcutaneous, intravenous particularly infusion, rectal and topical) use. These pharmaceutical compositions may be prepared by known methods, e.g. by sieving, mixing, granulating and compressing the components needed to the desired compositions. The compositions may be subjected to additional operations commonly used in the pharmaceutical industry such as coating the tablets, sterilization or the like.

The dose limits used of ethyl (+)-apovincaminate usually are between 0.05 and 50 mg/kg/day, optionally divided to two or more, portions per day preferably two portions. The dose depends in each case on the patient, the severity of the disease, route of administration and the like.

Specific Examples

The invention is illustrated in detail by the following non-limiting Examples.

EXAMPLE 1

Preparation of tablets containing ethyl (+)-apovincaminate

| Composition | mg |
| --- | --- |
| Ethyl (+)-apovincaminate | 5.00 |
| Colloidal silicic acid | 1.25 |
| Magnesium stearate | 2.50 |
| Talc | 5.00 |
| Starch | 96.25 |
| Lactose | 140.00 |
| | 250.00 |

The above-defined amount of the active ingredient is mixed with the above-defined amounts of the additives, the mixture obtained is homogenized, granulated, subjected to drying by fluidization and then compressed to tablets each of which weighs 250 mg and contains 5 mg of the active ingredient.

EXAMPLE 2

Preparation of an injectable solution containing ethyl (+)-apovincaminate

| Composition | mg |
| --- | --- |
| Ethyl (+)-apovincaminate | 10.00 |
| Ascorbic acid | 4.00 |
| Sodium pyrosulfate | 3.20 |
| Tartaric acid | 20.00 |
| Benzyl alcohol | 30.00 |
| Propylene glycol | 800.00 |

The above-defined amount of the active ingredient is mixed with the above-given additives and made up to 2 ml with distilled water. The solution is sterilized by filtration, filled into ampoules previously sterilized and sealed.

What is claimed is:

1. A method of treating demyelinization clinical patterns of autoimmune origin in an animal subject, which comprises administering to the subject a therapeutically effective amount of ethyl (+)-apovincaminate.

2. The method defined in claim 1 wherein the ethyl (+)-apovincaminate is administered by oral or intravenous route, in a daily dose of 0.05 to 50 mg/kg in at least one portion daily.

3. The method defined in claim 2 wherein the ethyl (+)-apovincaminate is administered by infusion.

4. The method defined in claim 2 wherein said daily dose is administered in at last two portions.

* * * * *